United States Patent
Montalbetti et al.

(10) Patent No.: US 12,291,526 B2
(45) Date of Patent: May 6, 2025

(54) DEUTERATED DERIVATIVES OF LANIFIBRANOR

(71) Applicant: INVENTIVA, Daix (FR)

(72) Inventors: Christian Montalbetti, Fontaine-les-Dijon (FR); Benaissa Boubia, Saint Apollinaire (FR)

(73) Assignee: INVENTIVA, Daix (FR)

( * ) Notice: Subject to any disclaimer, the term of this patent is extended or adjusted under 35 U.S.C. 154(b) by 768 days.

(21) Appl. No.: 17/261,938

(22) PCT Filed: Jul. 26, 2019

(86) PCT No.: PCT/FR2019/051860
§ 371 (c)(1),
(2) Date: Jan. 21, 2021

(87) PCT Pub. No.: WO2020/021215
PCT Pub. Date: Jan. 30, 2020

(65) Prior Publication Data
US 2021/0300913 A1    Sep. 30, 2021

(30) Foreign Application Priority Data
Jul. 27, 2018 (FR) ..................... 18 57021

(51) Int. Cl.
*C07D 417/12* (2006.01)

(52) U.S. Cl.
CPC ........ *C07D 417/12* (2013.01); *C07B 2200/05* (2013.01)

(58) Field of Classification Search
CPC .......................... C07D 417/12; C07B 2200/05
See application file for complete search history.

(56) References Cited

U.S. PATENT DOCUMENTS

| | | | | |
|---|---|---|---|---|
| 8,436,040 B2 * | 5/2013 | Binet | ................... | C07D 209/18 514/415 |
| 10,052,311 B2 * | 8/2018 | Konstantinova | ........ | A61P 11/00 |
| 11,504,380 B2 * | 11/2022 | Wettstein | ........... | A61K 31/5415 |

FOREIGN PATENT DOCUMENTS

| | | |
|---|---|---|
| WO | 2007/026097 | 3/2007 |
| WO | 2015/189401 | 12/2015 |
| WO | 2017/136375 | 8/2017 |
| WO | 2018/039521 | 3/2018 |

OTHER PUBLICATIONS

Laeter et al. Pure Appl. Chem., vol. 75, No. 6, pp. 683-800, 2003 (Year: 2003).*
S. Kaur et al., "Deuteration as a Tool for Optimization of Metabolic Stability and Toxicity of Drugs", Global Journal of Pharmacy & Pharmaceutical Science, 2017.
S. Harbeson et al., "Deuterium Medicinal Chemistry: A New Approach to Drug Discovery and Development", Medichem News, 2014.
Boubia et al., "Design, synthesis and . . . antifibrotic clinical candidate", Journal of Medicinal Chemistry, vol. 61, Feb. 15, 2018, pp. 2246-2265, XP002790345.
Katsnelson A., "Heavy drugs draw heavy interest from pharma backers", Nature Medicine, vol. 19, No. 6, Jun. 1, 2013, p. 656, XP002790346.

* cited by examiner

*Primary Examiner* — Clinton A Brooks
*Assistant Examiner* — Jerica Katlynn Wilson
(74) *Attorney, Agent, or Firm* — Christopher W. Brody; Millen, White, Zelano & Branigan, P.C.

(57) ABSTRACT

The present invention relates to deuterated derivatives of lanifibranor, in particular for use in therapy, specifically in the treatment of fibrotic diseases.

6 Claims, No Drawings

DEUTERATED DERIVATIVES OF LANIFIBRANOR

FIELD OF THE INVENTION

The present invention relates to deuterated derivatives of lanifibranor, in particular for their use in therapy, in particular in the treatment of fibrotic diseases.

STATE OF THE ART

Lanifibranor or 4-(1-(1,3-Benzothiazol-6-ylsulfonyl)-5-chloro-indol-2-yl)-butanoic acid is a PPAR receptor agonist useful in particular for its use in the treatment of systemic sclerosis (SSc) and in non-alcoholic steatohepatitis (NASH). Lanifibranor is in particular described with other indole derivatives in patent application WO 2007/026097, in particular for the prevention or treatment of hypertriglyceridemia, hypercholesterolemia and, more generally, for re-establishing normal parameters during disruption of lipid and carbohydrate metabolism, and also in the case of the treatment of endothelial dysfunction, inflammatory diseases or neurodegeneration.

The interest of using deuterated molecules is known as a means of modifying their metabolism by improving their metabolic stability and possibly their cell penetration properties (Maehr & al., J. Med. Chem. 2013, 56, 3878-3888; Kerekes et al., J. Med. Chem. 2011, 54, 201-210; Harbeson & Tung, Medchem News 2014, 2 9-22; Gant, J. Med. Chem. 2014, 57, 3595-3611; DeWitt & Maryanoff, Biochemistry 2018, 57, 472-473; WO 2017/136375; WO 2018/039521). The synthesis of deuterated drugs is also described in several articles (Modutwa & al., J. Label Compd. Radiopharm 2010, 53 686-692; Junk et al., J. Label Compd. Radkopharm 1997, 39 625-630).

However, it is recognized that the effect of hydrogen substitutions by deuteriums on the metabolism of chemicals remains unpredictable and for many authors deuteration of drugs is not considered a reliable means of modulation (Foster, AB, Adv Drug Res 1985, 14: 1-40; Fisher, M B et al, Curr Opin Drug Discov Devel, 2006, 9: 101-09; Katsnelson, Nature Medicine 2013, 19 6 656).

DESCRIPTION OF THE INVENTION

The invention relates to a deuterated derivative of lanifibranor of formula (I):

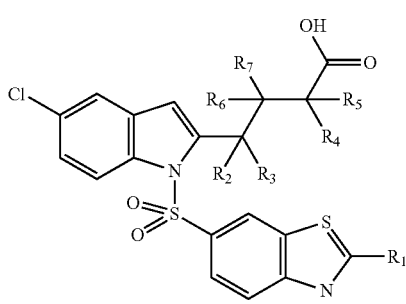

wherein at least one of the groups $R_1$ to $R_7$ is a deuterium atom (D) and the other groups $R_1$ to $R_7$ are hydrogen atoms (H).

The invention also relates to a composition, in particular a pharmaceutical composition, which comprises at least one deuterated derivative of formula (I).

The invention also relates to the deuterated derivatives of formula (I) for their use in therapy, in particular for the treatment of fibrotic diseases.

DETAILED DESCRIPTION OF THE INVENTION

The Invention relates to a deuterated derivative of lanifibranor of formula (I):

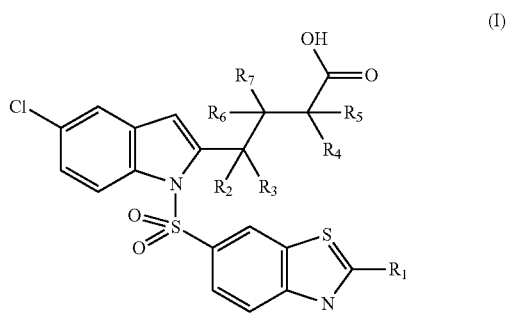

wherein at least one of the groups $R_1$ to $R_7$ is a deuterium atom and the other groups R, to $R_7$ are hydrogen atoms, and its pharmaceutically acceptable salts and solvates.

According to a first embodiment of the invention, at least the group $R_1$ is D.

In particular, the deuterated derivative of lanifibranor is 4-[1-[(2-deuterio-1,3-benzothiazol-6-yl)sulfonyl]-5-chloro-1H-indol-2-yl]butanoic acid.

According to another embodiment of the invention, at least one of the groups $R_2$ to $R_7$ is D. More preferably at least one of the groups $R_2$ and $R_3$ and/or at least one of the groups $R_4$ and $R_5$ and/or at least one of the groups $R_6$ and $R_7$ is D. Even more preferably, $R_2$, $R_3$, $R_4$, $R_5$, $R_6$ and $R_7$ are D.

In particular, the deuterated derivative of lanifibranor is 4-[1-(1,3-benzothiazol-6-ylsulfonyl)-5-chloro-indol-2-yl]-2,2,3,3,4,4-hexadeuteriobutanoic acid.

The pharmaceutically acceptable salts of the deuterated derivatives according to the invention are the same as the pharmaceutically acceptable salts of lanifibranor, in particular by combining the add with a pharmaceutically acceptable non-toxic inorganic or organic base. Among the inorganic bases, it is possible to use, for example, the hydroxides of sodium, potassium, magnesium or calcium. Among the organic bases, use may be made, for example, of amines, amino alcohols, basic amino acids such as lysine or arginine or else compounds carrying a quaternary ammonium function such as, for example, betaine or choline.

The compounds according to the invention are prepared according to the usual methods for preparing lanifibranor, for example that described in patent application WO 2007/026097, the deuterated synthesis intermediates replacing the same isotopically unenriched intermediates used in these usual methods.

The Invention also relates to a composition comprising a deuterated derivative according to the invention, or one of its salts or solvates, in particular a pharmaceutically acceptable salt or solvate, and a carrier suitable for its use.

For use in therapy, the composition according to the invention is advantageously a pharmaceutical composition, the carrier comprising usual excipients from the Pharmacopoeia, chosen according to the mode of administration envisaged.

Such compositions are known to those skilled in the art, and in particular described in patent applications WO 2007/026097 and WO 2015/189401.

For oral administration, for example in the form of a tablet, capsule, lozenge, gel, syrup, oral suspension, the pharmaceutical composition according to the invention advantageously comprises from 1 to 1000 mg of deuterated derivative of formula (I), for example 1 mg, 5 mg, 10 mg, 50 mg, 100 mg, 200 mg, 500 mg or 1000 mg.

The invention also relates to the deuterated derivatives of formula (I), or their pharmaceutically acceptable salts or solvates, for their use in therapy.

The different therapeutic uses of the deuterated derivatives according to the invention are those known for lanifibranor and its analogues, such as those described in patent applications WO 2007/026097 and WO 2015/189401.

The invention therefore relates to deuterated derivatives of formula (I), or their pharmaceutically acceptable salts or solvates, for their use to fight hypercholesterolemia, hyperlipidemia, hypertriglyceridemia, dyslipidemia, insulin resistance, diabetes or obesity as well as cardiovascular diseases which are the consequence of a serum lipoprotein imbalance. The compounds according to the invention are also useful as active principles of medicaments intended to prevent or treat diseases associated with an endothelial dysfunction, atherosclerosis, myocardial infarction, hypertension, cerebrovascular problems, certain inflammatory diseases such as example rheumatoid arthritis, and neurodegeneration such as in particular Alzheimer's disease or Parkinson's disease.

The invention relates in particular to the deuterated derivatives of formula (I) for their use in the treatment of fibrotic diseases. In one embodiment, fibrotic disease is a condition affecting any organ which can develop fibrosis, such as the heart, the lung, the liver, the kidney, the gastrointestinal tract, the skin, muscles, etc. The fibrotic disease is in particular chosen from: liver fibrosis, liver steatosis, non-alcoholic steatohepatitis, chronic kidney disease, a pulmonary fibrotic disorder such as idiopathic pulmonary fibrosis, and systemic sclerosis.

The invention also relates to a method of treating a fibrotic disease as defined above in a patient awaiting such treatment which comprises the administration to this patient of a deuterated derivative of formula (I), in particular by means of a pharmaceutical composition comprising said deuterated derivative of formula (I) in a form suitable for the chosen mode of administration.

The need for patient treatment will have advantageously been previously determined by any appropriate method of diagnosis for the detection of the fibrotic disease to be treated, in particular by the analysis of the expression levels of PPAR receptors in the fibrotic tissues of the patients to treat.

EXAMPLES

Abbreviations

APCI=atmospheric-pressure chemical ionization
DCM=dichloromethane
DMSO=dimethyl sulfoxide
eq.=equivalent
EtOAc=ethyl acetate
EtOH=ethanol
h=hour
HPLC=high performance liquid chromatography
LCMS=liquid chromatography coupled with mass spectrometry
MeOH=methanol
min=minute
Pd(PPh$_3$)$_4$=tetrakis(triphenylphosphine)palladium(0)
pTsOH=paratoluenesulfonic acid
NMR=nuclear magnetic resonance
THF=tetrahydrofuran Example 1: 4-[5-Chloro-1-[(2-deuterio-1,3-benzothiazol-6-yl)sulfonyl)]indol-2-yl]butanoic acid Preparation 1: 2-Deuterio-1,3-benzothiazaole n-BuLi (37.0 ml, 92.5 mmol, 2.5 eq; 2.5 M solution in hexane) was added dropwise to 1,3-benzothiazole (5.0 g, 36.9 mmol, 1.0 eq.) dissolved in THF (80 mL), and cooled to −78° C. After complete addition, D$_2$O (4 mL, 222 mmol, 6.0 eq.) was added to the reaction mixture at −78° C., the whole was stirred for 30 min then brought to room temperature. The reaction was monitored by LCMS analysis. The reaction mixture was then treated with a saturated aqueous NH$_4$Cl solution and the whole was extracted 3 times with DCM. The organic phases were combined and dried over MgSO, then filtered and evaporated under reduced pressure to yield a crude product purified by flash chromatography (eluent: 0 to 40% EtOAc in n-heptane) to give the compound of preparation 1 (3.22 g, 64% yield) as a brown oil. APCI MS m/z 137 [M+H]$^+$; HPLC-MS (220-254 nm) purity: 99%. $^1$H NMR (300 MHz DMSO-d$_6$): δ 7.46-7.58 (2H, m); 8.08-8.19 (2H, m).

Preparation 2: 2-Deuterio-6-nitro-1,3-benzothiazole

2-Deuterio-1,3-benzothiazole (preparation 1, 2.9 g, 21.3 mmol, 1.0 eq.) was added slowly to a solution of sulfuric acid (13 mL) at 0° C., nitric acid (6.4 mL) was then added dropwise while maintaining the temperature below 0° C. The reaction mixture was then brought to room temperature and stirred for 12 h before being hydrolysed over a mixture of iced water. The yellow precipitate was filtered off, washed with water and crystallized from ethanol to yield the desired product (preparation 2, 1.4 g, yield 37%) in the form of yellow crystals. APCI MS m/z 182 [M+H]$^+$; HPLC-MS (220-254 nm) purity>99%. $^1$H NMR (300 MHz DMSO-d6): δ 8.27-8.38 (2H, m); 9.25 (1H, d, J=2.3 Hz).

Preparation 3: 2-Deuterio-1,3-benzothiazol-6-amine

Tin chloride powder (7.3 g, 38.6 mmol, 3.5 eq.) was added to the compound of preparation 2 (2.0 g, 11.0 mmol, 1.0 eq.) dissolved in a 1:1 EtOH-EtOAc mixture (60 mL), and the solution was stirred at room temperature for 4 h. At the end of the reaction, the reaction mixture was filtered through a Celite™ cartridge and extracted with a saturated Na$_2$CO$_3$ solution. The organic phases were combined and dried over MgSO$_4$ then filtered and evaporated under reduced pressure to yield a crude product purified by flash chromatography (eluent: 0 to 20% MeOH in DCM) to obtain the desired compound (preparation 3, 970 mg, yield 58%) as brown crystals. APCI MS m/z 152 [M+H]$^+$; HPLC-MS (220-254 nm) purity: 97%. $^1$H NMR (300 MHz DMSO-d6): δ 5.38 (211, s); 6.8 (1H, dd, J=8.7 Hz and J=2.2 Hz); 7.11 (1H, d, J=2.2 Hz); 7.7 (1H, d, J=8.7 Hz).

Preparation 4:
2-Deuterio-1,3-benzothiazol-6-sulfonyl chloride

An aqueous solution (4.5 mL) of thionyl chloride (1.1 mL) was prepared at 0° C. and stored overnight at 4° C. To this solution copper (I) chloride (0.05 eq.) was added at −10° C. The compound of preparation 3 (450 mg, 2.9 mmol, 1.0 eq.) was dissolved in hydrochloric acid (3.5 mL) while maintaining the temperature below 25° C., the latter solution having then been cooled to −10° C. and a solution of sodium nitrite (3.3 mmol, 0.7 mL, 1.1 eq.) was added without the temperature exceeding −2° C. The mixture thus obtained was stirred for 15 min at −2° C. and then added dropwise to the first solution of thionyl chloride at −5° C. The reaction mixture was then stirred at −5° C. for 3 h then the reaction was hydrolysed in water. The precipitate formed was filtered and then washed with water to yield the desired product (preparation 4, 255 mg, yield 37%) in the form of light brown crystals. This compound was used in the next step without any purification. HPLC-MS (220-254 nm) purity: 94%.

Preparation 5: N-(4-Chloro-2-iodophenyl)-2-deuterio-1,3-benzothiazole-6-sulfonamide Under argon, 4-chloro-2-iodoaniline (564 mg, 2.2 mmol, 1.0 eq.) was dissolved in anhydrous pyridine (8 mL) and the compound of preparation 4 (600 mg, 2.5 mmol, 1.15 eq.) was added. The solution was then stirred at room temperature for 2 h. The solvent was evaporated and the reaction crude was purified by flash chromatography (eluent: 0 to 30% EtOAc in n-heptane) to yield the desired product (preparation 5, 0.73 g, yield 73%) in the form of brown crystals. APCI MS m/z 452 [M+H]$^+$; HPLC-MS (220-254 nm) purity: 94%. $^1$H NMR (300 MHz DMSO-d6): δ 7.01 (1H, d, J=8.5 Hz); 7.4 (1H, dd, J=8.5 Hz and J=2.3 Hz); 7.82 (1H, dd, J=8.7 Hz and J=1.8 Hz); 7.88 (1H, d, J=2.4 Hz); 8.26 (1H, d, J=8.7 Hz); 8.6 (1H, d, J=1.5 Hz); 10.03 (1H, s).

Preparation 6: 4-[5-Chloro-1-[(2-deuterio-1,3-benzothiazol-6-yl)sulfonyl)]indol-2-yl]butanoic acid Under argon the compound of preparation 5 (1.31 g, 2.9 mmol, 1.0 eq.) was dissolved in anhydrous DMF (30 mL), then 5-hexynoic acid (360 mg, 3.2 mmol, 1.1 eq.), copper iodide (56 mg, 0.3 mmol, 0.1 eq.), Pd(PPh$_3$)$_4$ (168 mg, 0.15 mmol, 0.05 eq.) and triethylamine (606 µL, 4.4 mmol, 1.5 eq.) were added and the reaction mixture was stirred at 80° C. for 2 h. At the end of the reaction, the mixture was taken up in a 1N aqueous hydrochloric acid solution and extracted twice with ethyl acetate. The organic phases were combined and dried over MgSO$_4$ then filtered and evaporated under reduced pressure to yield a crude product purified by flash chromatography (eluent: 0 to 5% MeOH in DCM) to yield the desired product (Example 1, 1.05 g, yield 83%) in the form of brown crystals. APCI MS m/z 452 [[M+H]$^+$; HPLC-MS (220-254 nm) purity: 94%. $^1$H NMR (300 MHz DMSO-d6): δ 1.86-2.01 (2H, m); 2.29-2.41 (2H, m); 3.08 (2H, t, J=7.2 Hz); 6.61 (1H, s); 7.31 (1H, dd, J=8.7 Hz and J=2.0 Hz); 7.51 (1H, d, J=2.0 Hz); 7.84 (1H, dd, J=8.7 Hz and J=1.8 Hz); 8.08 (1H, d, J=8.7 Hz); 8.19 (1H, d, J=8.7 Hz); 8.97 (1H, d, J=1.8 Hz); 12.13 (1H, s). Incorporation rate of deuterium assayed by 500 MHz NMR: 98%.

Example 2: 4-[1-(1,3-Benzothiazol-6-ylsulfonyl)-5-chloro-indol-2-yl]-2,2,3,3,4,4-hexadeuteriobutanoicacid Preparation 7: 2-(1,1,2,2,3,3,4,4-octadeutério-4-iodo-butoxy)tetra-hydropyrane Trimethylsilyl iodide (25 g, 125 mmol, 1 eq.) was added at 0° C. to THF-D8 (10 g, 125 mmol, 1 eq.). After stirring for 2 h at 0° C., ether (80 mL) and water (20 mL) were added. The mixture was stirred for 3 h then decanted. The organic phase was then dried over MgSO$_4$, filtered and concentrated under reduced pressure. The reaction crude thus obtained was taken up in DCM (100 mL) at 0° C., then dihydropyran (12.5 mL, 150 mmol, 1.2 eq.) and pTsOH (50 mg, 0.2 mmol, 0.002 eq.) were added. The reaction mixture was then stirred at 0° C. overnight. The solution was washed successively with a saturated solution of NaHCO$_3$ (3×15 mL), then with brine and then dried over Na$_2$SO$_4$ before being concentrated under reduced pressure. The reaction crude was purified by flash chromatography (eluent: 1:20 to 1:5 EtOAc:Hexane) to yield the desired product (Preparation 7, 23 g, 62% yield) in the form of a colourless oil which was used directly in the next step.

Preparation 8: 2-(1,1,2,2,3,3,4,4-octadeuteriohex-5-ynoxy)tetrahydropyran

To a solution of lithium acetylide (19.94 g, 186.3 mmol, 1 eq.) in freshly distilled DMSO (60 mL) was added dropwise at 5° C. a solution of the compound of preparation 7 (30 g, 102.7 mmol, 0.55 eq.) in DMSO (30 mL). This solution thus obtained was stirred for 2 h then hydrolysed with a solution of NH$_4$Cl at 0° C. This mixture was then extracted with hexane and washed with a solution of copper sulfate (5%, 20 mL) then with brine (20 mL). The organic phases were combined and dried over Na$_2$SO$_4$ before being concentrated under reduced pressure, to yield the desired product (Preparation 8, 10.7 g, yield 55%) in the form of a yellow oil which was used directly in the next step without any purification.

Preparation 9:
1,1,2,2,3,3,4,4-octadeuteriohex-5-yn-1-ol

To a solution of the compound of preparation 8 (10.7 g, 56.2 mmol, 1 eq.) in a mixture of THF (12.5 mL) and MeOH (350 mL) at 0° C., was added pTsOH in small portions (360 mg, 1.82 mmol, 0.03 eq.) and the reaction mixture thus obtained was stirred overnight. The mixture was then washed with a saturated solution of NaHCO$_3$ (3×15 mL) and brine (15 mL), then dried over Na$_2$SO$_4$ before being concentrated under reduced pressure. The reaction crude was purified by flash chromatography (eluent: 1:20 to 1:5 EtOAc:Hexane) to yield the desired product (Preparation 9, 5 g, 82% yield) in the form of a colourless oil which was used directly in the next step.

Preparation 10: 2,2,3,3,4,4-hexadeuteriohex-5-ynoic acid

To a solution of the compound of preparation 9 (9.25 g, 87 mmol, 1 eq.) in acetone (87 mL) was added, under stirring, Jones's reagent (CrO$_3$(17.45 g, 174.5 mmol, 2 eq.) in 10N H$_2$SO$_4$ (218 mL)) over 5 min at 0° C. The reaction mixture was then stirred for 1 h before being concentrated under reduced pressure. Then ether (130 mL) and water (4 mL) were added immediately. The solid obtained was filtered off and the filtrate was extracted with ether (6×100 mL). The organic phases were combined and washed with water and then dried over $Na_2SO_4$ before being filtered and concentrated under reduced pressure to yield the desired product (Preparation 10, 9.17 g, yield 89%) in the form of an orange oil which was used directly in the next step without any purification.

Preparation 11: 4-[1-(1,3-Benzothiazol-6-ylsulfonyl)-5-chloro-Indol-2-yl]-2,2,3,3,4,4-hexadeuteriobutanoic acid A mixture of benzothiazol-6-sulfonic acid (4-chloro-2-iodo-phenyl)-amide (16 g, 35.5 mmol, 1 eq.), hex-5-ynoic acid (preparation 10, 5.2 g, 44 mmol, 1.24 eq.), copper iodide (335 mg, 1.75 mmol, 0.05 eq.), dichlorobis(triphenylphosphine)palladium (1.24 g, 1.72 mmol, 0.05 eq.), triethylamine (130 mL) and N,N-dimethylformamide (130 mL) was stirred under nitrogen at 110° C. for 1 h. The reaction mixture was then diluted with a 1M HCl solution and extracted with ethyl acetate, the insoluble matters were filtered off and the filtrate was dried over $Na_2SO_4$ before being concentrated under reduced pressure. The reaction crude was purified by flash chromatography and then recrystallized from DCM to yield the desired product (Example 2, 2.3 g, yield 15%) in the form of a white solid. Incorporation rate of deuterium assayed by 500 MHz NMR: >99%. $^1$H NMR (400 MHz, DMSO-d6) δ 6.62 (1H, d, J=0.6 Hz), 7.32 (1H, dd, J=8.9 and 2.2 Hz), 7.57 (1H, d, J=2.1 Hz), 7.85 (1H, dd, J=8.7 and 2.1 Hz), 8.10 (1H, d, J=8.9 Hz), 8.20 (1H, d, J=8.7 Hz), 8.99 (1H, s), 9.66 (1H, s), 12.15 (1H, s).

Example 3: Pharmacological Activity

The compounds of the invention were subjected to biological tests so as to evaluate their potential to treat or prevent certain pathologies. First, the ability of the compounds to behave as an activator of PPAR nuclear receptors was measured.

A transactivation test was used as the primary screening test. Cos-7 cells were transfected with a plasmid expressing a chimera of a murine or human receptor PPAR-Gal4 (receptor PPARα-Gal4 or PPARδ-Gal4 or PPARγ-Gal4) and of a reporter plasmid 5Gal4pGL3 TK Luc. The transfections were carried out using a chemical agent (Jet PEI). Transfected cells were distributed into 384 well plates and allowed to stand for 24 hours. At 24 hours the culture medium was changed. The products to be tested were added (final concentration between $10^{-4}$ and $3.10^{-10}$ M) to the culture medium. After overnight incubation, luciferase expression was measured after addition of "SteadyGlo" according to the manufacturer's instructions (Promega).

Fenofibric acid at $10^{-5}$ M (PPARα agonist), GW501516 at $10^{-8}$ M (PPARδ agonist) and rosiglitazone at $10^{-6}$ M (PPARγ agonist) were used as references.

The results are expressed as the induction rate (number of times) compared to the basal level as a percentage of activity of the adequate reference (reference=100%). Effect-concentration curves and $EC_{50}$ were calculated using Assay Explorer (MDL) software.

TABLE 1

| Human receptor | PPARα | | PPARδ | | PPARγ | |
|---|---|---|---|---|---|---|
| Example | $EC_{50}$ (nM) | Top(%) | $EC_{50}$ (nM) | Top(%) | $EC_{50}$ (nM) | Top(%) |
| 1 | 2317 | 67 | 952 | 80 | 85 | 53 |
| 2 | 2280 | 62 | 1177 | 80 | 136 | 50 |

As can be seen from the table above, the deuterated derivatives of lanifibranor activate the three subtypes of PPAR receptors (PPARα, PPARγ and PPARδ), with an $EC_{50}$ of less than 2.5 μM for each of the sub-types. It can also be noted that the ratio between the $EC_{50}$ of two PPAR subtypes is either less than 100 or greater than 0.01.

REFERENCES

1. DeWitt & Maryanoff, Biochemistry 2018, 57, 472-473
2. Fisher et al, Curr Opin Drug Discov Devel, 2006, 9: 101-09
3. Foster, Adv Drug Res 1985, 14: 1-40
4. Gant, J. Med. Chem. 2014, 57, 3595-3611
5. Harbeson & Tung, Medchem News 2014, 2 9-22
6. Junk et al., J. Label Compd. Radiopharm 1997, 39 625-630
7. Katsnelson, Nature Medicine 2013, 19 6 656
8. Kerekes et al., J. Med. Chem. 2011, 54, 201-210
9. Maehr et al., J. Med. Chem. 2013, 56, 3878-3888
10. Modutwa & al., J. Label Compd. Radiopharm 2010, 53 686-692
11. WO 2007/026097
12. WO 2015/189401
13. WO 2017/136375
14. WO 2018/039521

The invention claimed is:

1. A deuterated derivative of lanifibranor, which is 4-[1-[(2-deuterio-1,3-benzothiazol-6-yl)sufonyl]-5-chloro-1H-indol-2-yl]butanoic acid.

2. A composition which comprises a deuterated derivative of claim 1 or one of its salts or solvates, and a suitable carrier.

3. A pharmaceutical composition which comprises a deuterated derivative of claim 1, or a pharmaceutically acceptable salt or solvate thereof, and a pharmaceutically acceptable carrier.

4. A method of treating a fibrotic disease which comprises administering. to a subject in need thereof.

5. The method of claim 4, wherein the fibrotic disease is selected from the group consisting of liver fibrosis, liver steatosis, non-alcoholic steatohepatitis, chronic kidney disease, a pulmonary fibrotic disorder, and systemic sclerosis.

6. The method of claim 5, wherein the fibrotic disease is non-alcoholic steatohepatitis.

* * * * *